(12) United States Patent
Aronhime et al.

(10) Patent No.: US 6,586,576 B2
(45) Date of Patent: Jul. 1, 2003

(54) PREPARATION METHOD OF AZITHROMYCIN HYDRATES

(75) Inventors: Judith Aronhime, Rechovot (IL); Claude Singer, Kfar Saba (IL); Michael Pesachovich, Givat Shmuel (IL)

(73) Assignee: Teva Pharmaceutical Industries LTD, Petah Tiqva (IL)

( * ) Notice: Subject to any disclaimer, the term of this patent is extended or adjusted under 35 U.S.C. 154(b) by 0 days.

(21) Appl. No.: 09/755,829

(22) Filed: Jan. 4, 2001

(65) Prior Publication Data

US 2001/0047089 A1 Nov. 29, 2001

Related U.S. Application Data

(60) Provisional application No. 60/220,681, filed on Jul. 25, 2000, and provisional application No. 60/174,330, filed on Jan. 4, 2000.

(51) Int. Cl.⁷ ............................. C07H 17/08; C07H 1/00
(52) U.S. Cl. ..................... 536/7.4; 536/18.5; 536/127
(58) Field of Search ................... 536/7.5, 18.5, 536/127, 7.4

(56) References Cited

U.S. PATENT DOCUMENTS

| 4,474,768 A | 10/1984 | Bright |
| 4,517,359 A | 5/1985 | Kobrehel et al. |
| 4,963,531 A | 10/1990 | Remington |

FOREIGN PATENT DOCUMENTS

| EP | 298 650 | 1/1989 |
| EP | 298 650 B1 | 2/1992 |
| EP | 941 999 A2 | 9/1999 |
| JP | 93120880.7 | 12/1994 |

*Primary Examiner*—Elli Peselev
(74) *Attorney, Agent, or Firm*—Kenyon & Kenyon

(57) ABSTRACT

This invention relates to a method for preparing azithromycin dihydrate from crude azithromycin by the gradual crystallization of azithromycin from acetone by the addition of a minimal amount of water to effect crystal formation is disclosed. This invention also relates to a method of making azithromycin from desmethyl-azithromycin by dissolving desmethyl-azithromycin in acetone, adding activated carbon, adding formaldehyde, adding formic acid; refluxing the desmethyl-azithromycin acetone solution, adding sodium hydroxide to induce precipitation of azithromycin, and isolating azithromycin.

37 Claims, No Drawings

PREPARATION METHOD OF AZITHROMYCIN HYDRATES

CROSS-REFERENCE TO RELATED APPLICATIONS

This application claims the benefit of provisional applications Ser. Nos. 60/174,330, filed Jan. 4, 2000; and 60/220,681, filed Jul. 25, 2000.

FIELD OF THE INVENTION

This invention relates to methods of preparing antibiotics, and more particularly to a new method for the crystallization of azithromycin dihydrate.

BACKGROUND OF THE INVENTION

Azithromycin, 9-deoxo-9a-aza-9a-methyl-9a-homoerythromycin A, has the structural formula

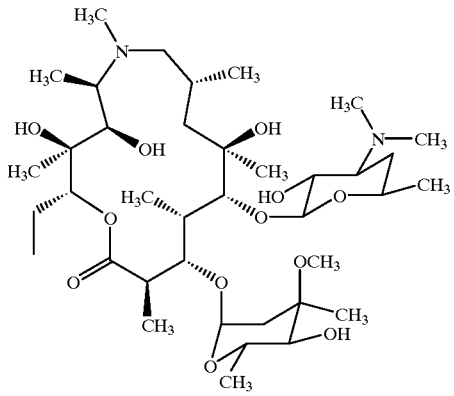

and is a semi-synthetic macrolide antibiotic related to erythromycin A. Azithromycin possesses broad-antibacterial activity, and is useful for treating infections caused by susceptible microorganisms.

U.S. Pat. Nos. 4,517,359 and 4,474,768 describe methods for the preparation of azithromycin. According to European Patent Application EP 298 650 ("the EP '650 application"), the azithromycin obtained by the methods of U.S. Pat. Nos. 4,517,359 and 4,474,768 is a hygroscopic monohydrate. Because of its hygroscopic nature, the azithromyycin monohydrate is difficult to prepare and maintain in a form having a constant, reproducible water-content, and is particularly difficult to handle during formulation. The EP '650 application describes a dihydrate form of azithromycin that is less hygroscopic than the previously known azithromycin monohydrate. The method described in the EP '650 application for making the dihydrate form from the monohydrate is by crystallization from tetrahydrofuran, hexane and water. It would be advantageous to be able to manyfacture azithromycin dihydrate by a process which uses less potentially toxic solvents.

Chinese Patent Application CN 1,093,370 ("the Chinese '370 application") describes an azithromycin crystal having water content of 4–6% and is characterized therein as being less hygroscopic than the dihydrate described in the EP '650 application. The method disclosed in the Chinese '370 application for making the described form of azithromycin is by crystallization from acetone and water.

A solvent system of acetone and water is also described in the European Patent application 941,999 wherein azithromycin dihydrate is precipitated from the acid salt by the addition of base. It is known from the relevant literature that azithromycin is not stable under acidic conditions and therefore potential undesirable impurities may be obtained by the precipitation method described by the EP '999 application.

Thus, there remains a need for a method of making azithromycin dihydrate in high yields directly from crude azithromycin (without the need to first isolate the monohydrate), under non-acidic conditions which does not necessitate the use of solvent which have potential toxicity problems in the production of pharmaceutical products.

By conventional methods of manufacture, azithromycin may contain isomers of azithromycin in about 0.5% to about 1%. It would be advantageous to have a method of removing possible isomers from azithromycin such that the purity of azithromycin dihydrate may be enhanced.

By conventional methods of manufacture, azithromycin may contain an impurity which is a derivative of azithromycin. It would be advantageous to have a method of making azithromycin which is substantially free of impurities that are derivatives of azithromycin.

SUMMARY OF THE INVENTION

The present invention relates to a process for making azithromycin dihydrate, comprising the steps of: (a) dissolving azithromycin in acetone; (b) maintaining the solution of azithromycin and acetone temperature of about 20° C. to about 25° C.; (c) adding water in two separate sequential additions, a first addition of water and a second addition of water; (d) adding water in the second addition step at a rate of up to 0.2 volumes of water per volume of acetone per hour; and (e) isolating the crystals of azithromycin dihydrate. Preferably, between about 0.4 to about 0.5 volumes of water per volume of water are added in the first addition of water. Preferably, the first addition of the water occurs over about 2 to about 3 hours. Preferably, the solution formed after the first addition of water is stirred for about 4 hours prior to the second addition of water. Preferably, the isolated azithromycin dihydrate contains less than 0.1% of isomers of azithromycin. More preferably, the isolated azithromycin dihydrate contains less than about 0.05 to about 0.02% of isomers of azithromycin. Most preferably, the isolated azithromycin dihydrate is substantially free of isomers of azithromycin.

The present invention relates to a method of making azithromycin from desmethyl-azithromycin comprising the steps of: (a) dissolving desmethyl-azithromycin in acetone; (b) refluxing the desmethyl-azithromycin acetone solution; (c) adding formaldehyde; (d) adding formic acid; (e) adding activated carbon; (f) adding sodium hydroxide to induce precipitation of azithromycin; and isolating azithromycin. Preferably, the isolated azithromycin is substantially free of derivatives of azithromycin.

The methods of the present invention are thus useful for the manufacture of azithromycin dihydrate in high yield and purity.

DETAILED DESCRIPTION OF THE INVENTION

The present invention provides new processes for the manufacture of azithromycin dihydrate wherein azithromycin dihydrate is made directly from crude azithromycin, under non-acidic conditions in unexpectedly high yields. Azithromycin for use as a starting material in the presently claimed method may be prepared according to the methods set forth in U.S. Pat. Nos. 4,517,359 and 4,474,768, the contents of which are incorporated herein by reference.

It has been discovered that in making azithromycin dihydrate by crystallization from acetone and water, that both (i) the temperature for the addition of water to a solution of acetone and azithromycin, and (ii) the addition profile for water during the precipitation process are essential. Further, it has been discovered that the present process for making azithromycin dihydrate, the purity of azithromycin is enhanced by the removal of isomers of azithromycin that may be present in the starting material.

Specifically, it has been discovered that for the precipitation of azithromycin dihydrate from acetone and water, the optimal temperature for addition of the water is from about 20° C. to about 25° C.; and that prior to precipitation of azithromycin dihydrate, about 0.4 to about 0.5 volumes of water to about 1 volume of acetone are added to the acetone solution over a time period of at least 2 hours. Additional water should be added only after definite crystals of azithromycin dihydrate are observed. The addition profile for water includes two separate sequential additions of water, a first addition of water, and a second addition of water. The final ratio of acetone:water should about 0.5 to about 1.5, preferably, not less than 1:1.

By the process of the present invention, azithromycin is dissolved in acetone. The temperature of the azithromycin solution is maintained at a range of about 20° C. to about 25° C. Preferably, the temperature is maintained at about 20° C. In the first addition of water to the acithromycin solution, water is added to the azithromycin solution with stirring such that crystallization of the azithromycin begins and a suspension is formed. The azithromycin solution formed following the first addition of water is stirred for at least two hours, preferably the reaction is stirred for about 2 to about 3 hours. Preferably, during the first addition of water, about 0.4 to about 0.5 volumes of water are added per volume of acetone to induce formation of a suspension. The resulting suspension is stirred until definite crystals of azithromycin dihydrate are observed and before any additional water is added. Preferably, the suspension which forms after the first addition of water is stirred for about 4 hours before additional water is added. After the suspension is formed, there is a second addition of water wherein water is added to complete the formation of azithromycin dihydrate crystals at a rate of up to 0.2 volumes of water per volume of acetone per hour after the suspension is formed. Azithromycin dihydrate is isolated by filtration followed by drying. The present method provides for high isolated yields of azithromycin dihydrate of greater than 90%.

The addition profile of water of the present invention provides for the formation of pure azithromycin dihydrate substantially free of azithromycin monohydrate. The unique temperature range maintained by the present invention prevents formation of azithromycin monohydrate which would occur at temperatures of greater than 35° C. Additionally, the unique addition rate of water of the present invention ensures the formation of azithromycin dihydrate in contrast to where the addition rate is less than 2 hours, which yields azithromycin monohydrate. Further, the methods of the present invention provides for a final ratio of acetone to water of not less than 1:1 which provides for high yields of azithromycin dihydrate crystals.

Azithromycin used as the starting material for the present invention may contain isomers of azithromycin in the amount of about 0.5% to about 1%. The methods of the present invention for making azithromycin dihydrate further purify the azithromycin by reducing the present of isomers of azithromycin in the isolated azithromycin dihydrate. Preferably, the isomers of azithromycin in the isolated azithromycin dihydrate are present in less than about 0.1%. More preferably, the isomers of azithromycin in the isolated azithromycin dihydrate are present in less than about 0.05% to about 0.02%. Most preferably, the isolated azithromycin dihydrate is substantially free of isomers of azithromycin dihydrate.

The present invention provides new processes for the manufacture of azithromycin from desmethyl-azithromycin. Desmethyl-azithromycin is also referred to in the art as 11-aza-10-deoxo-dihydroerythromycin A. Desmethyl-azithromycin for use as a starting material in the presently claimed method may be prepared according to the methods set forth in U.S. Pat. No. 4,517,359, the contents of which are incorporated herein by reference.

It has been discovered that azithromycin may contain an impurity which is a derivative of azithromycin. The present invention provides methods for the manufacture of azithromycin from desmethyl-azithromycin in which the resulting azithromycin is substantially free of impurities which are azithromycin derivatives.

By the methods of the present invention, desmethyl-azithromycin is dissolved in acetone. Formaldehyde and formic acid are added to the solution and the clear solution is heated to reflux (~58° C.). The mixture is maintained under reflux for about 3 hours then cooled to less than about 40° C. Water is added and the acetone is separated from the reaction mixture by distillation under low vacuum (~300 mbar). The distillation is stopped when the temperature of the liquid phase reaches ~40° C./300 mbar. Activated carbon SXI is added and the suspension is mixed for about 1 hour. The activated carbon is then separated from the solution by filtration on a Büchner filter containing Hyflow. The filter cake is washed with water. The pH is adjusted with an NaOH to about 10–10.5 to induce precipitation of azithromycin. The azithromycin suspension is stirred for about 1 hour. The crude azithromycin crude is separated by filtration and washed. Azithromycin is isolated upon drying the filtrate 40° C. in a vacuum oven. Preferably the azithromycin is dried for at least 24 hours. No impurities were detected that were derivatives of azithromycin in the isolated azithromycin Azithromycin dihydrate prepared in accordance with the present invention is suitable formulation and administration for the treatment of susceptible bacterial infections in humans according to the methods and in the amounts set forth in U.S. Pat. No. 4,474,768, cited above.

This invention will be better understood from the Example that follows. However, the example illustrates, but does not limit, the invention. Those skilled in the art will readily appreciate that the specific methods and results discussed are merely illustrative of the invention as described more fully in the claims that follow thereafter.

EXAMPLES

Example 1 Preparation of azithromycin dihydrate

Crude azithromycin, 50 g, was dissolved in 250 mL of acetone at 20° C. Water (100 mL) was added at 20° C. over a period of 3 hours. The addition of water was stopped and the solution was mixed for 4 hours. During this time interval the initial turbidity of the solution is transformed into a clear defined suspension. Water (150 mL) was added at 20° C. over a period of 3 hours. After drying, 45.65 g of azithromycin dihydrate was obtained with a yield of 91.3% based on weight.

Example 2 Preparation of azithromycin from Desmethyl-azithromycin

In a 0.25 L three-necked round bottom flask equipped with a mechanical stirrer, a condenser and thermometer, 25 g of desmethyl-azithromycin was dissolved in 102 mL of acetone. Formaldehyde (5.3 mL) and formic acid (2.6 mL) were added and the clear solution was heated to reflux (~58° C.). The mixture was maintained under reflux for 3 hours then cooled to less than 40° C. and 102 mL of water was added. The acetone was separated from the reaction mixture by distillation under low vacuum (~300 mbar). The distillation was stopped when the temperature of the liquid phase reaches ~40° C./300 mbar. Activated carbon SXI (1.25 g) was added and the suspension was mixed for 1 hour. Then the activated carbon was separated from the solution by filtration on a Büchner filter containing Hyflow. The filter cake was washed with 102 mL of water. The pH was adjusted with an NaOH solution of 47% to 10–10.5 (~3.14 g). A massive precipitation of Azithromycin was observed. After stirring the suspension for 1 hour, the crude azithromycin was separated by filtration, washed twice with 25 mL of water and dried at 40° C. in a vacuum oven for>24 hours. After drying, 19.7 g of crude azithromycin was obtained (yield 77% based on weight). No impurities that were derivatives of azithromycin were detected.

Example 3 Preparation of azithromycin monohydrate

Crude azithromycin (10 g) was dissolved in 50 mL of acetone at 20° C. Water (10 ml) was added at 20° C. over 1 hour. The addition of water was stopped and the solution was heated to 40° C. and maintained at 40° C. for about a half hour. Over a 2 hour time period, 20 mL of water was added at 40° C. During the addition of water the precipitation of azithromycin monohydrate started. An additional 20 mL of water was added during the next half-hour. The suspension was cooled over 1½ hours to 20° C. After filtration and drying, 9.38 g of azithromycin monohydrate was obtained. No azithromycin dihydrate was observed.

Although certain presently preferred embodiments of the invention have been described herein, it will be apparent to those skilled in the art to which the invention pertains that variations and modifications of the described embodiments may be made without departing from the spirit and scope of the invention. Accordingly, it is intended that the invention be limited only to the extent required by the appended claims and the applicable rules of law.

We claim:

1. A method of making azithromycin from desmethyl-azithromycin comprising the steps of:
   (a) dissolving desmethyl-azithromycin in acetone;
   (b) refluxing the desmethyl-azithromycin acetone solution;
   (c) adding formaldehyde;
   (d) adding formic acid;
   (e) adding activated carbon;
   (f) adding sodium hydroxide to induce precipitation of azithromycin; and isolating azithromycin.

2. The method of claim 1 wherein the isolated azithromycin is substantially free of derivatives of azithromycin.

3. The method of claim 1 further comprising the step of heating the desmethyl-azithromycin acetone solution.

4. The method of claim 1, wherein the desmethyl-azithromycin acetone solution is heated to reflux.

5. The method of claim 1 further comprising the step of drying azithromycin at about 40° C.

6. A process for making azithromycin dihydrate comprising:
   dissolving azithromycin in acetone;
   adding a first portion of water to the acetone to form a mixture;
   maintaining the mixture, with optional mixing, until definite crystals of azithromycin dihydrate are observed; and
   adding a second portion of water to the mixture.

7. The process of claim 6, further comprising recovering the azithromycin dihydrate.

8. The process of claim 6, wherein the temperature of the mixture is from about 20° C. to about 25° C.

9. A process for making azithromycin dihydrate comprising:
   dissolving azithromycin in acetone;
   adding a first portion of water to the acetone over at least 2 hours to form a mixture; and
   adding a second portion of water to the mixture.

10. The process of claim 6, wherein the mixing step continues for at least about 4 hours.

11. The process of claim 6, wherein the dissolved azithromycin is an azithromycin monohydrate.

12. The process of claim 6, wherein the ratio of the volume of the first portion of water to the volume of the solvent ranges from about 0.4 to 0.5.

13. The process of claim 6, wherein the ratio of the volume of the solvent to the total volume of water, after the step of adding the second portion of water, ranges from about 0.5 to about 1.5.

14. The process of claim 13, wherein the ratio of the volume of the solvent to the total volume of water, after the step of adding the second portion of water, ranges from about 1 to about 1.5.

15. The process of claim 6, wherein the azithromycin dihydrate contains less than about 0.1% isomers of azithromycin.

16. The process of claim 6, wherein the azithromycin dihydrate contains less than about 0.05% isomers of azithromycin.

17. The process of claim 6, wherein the azithromycin dihydrate contains less than about 0.02% isomers of azithromycin.

18. The process of claim 6, wherein the yield of azithromycin dihydrate is greater than 90%.

19. An azithromycin dihydrate composition having less than about 0.1% isomers of azithromycin.

20. The azithromycin dihydrate composition of claim 19, wherein the azithromycin dihydrate contains less than about 0.05% isomers of azithromycin.

21. The azithromycin dihydrate composition of claim 19, wherein the azithromycin dihydrate contains less than about 0.02% isomers of azithromycin.

22. A formulation comprising azithromycin dihydrate having less than about 0.1% isomers of azithromycin.

23. The formulation of claim 22, wherein the azithromycin dihydrate contains less than about 0.05% isomers of azithromycin.

24. The formulation of claim 22, wherein the azithromycin dihydrate contains less than about 0.02% isomers of azithromycin.

25. A process for making azithromycin from desmethyl-azithromycin comprising:
   admixing desmethyl-azithromycin, acetone, formaldehyde and formic acid to form a first mixture in which the desmethyl-azithromycin is dissolved;
   heating the first mixture;
   adding water to the first mixture to form a second mixture; and
   recovering the azithromycin.

26. The process of claim 25, wherein the first mixture is heated to between 40° C. and the reflux temperature of the first mixture and wherein the first mixture is cooled to less than about 40° C. after the heating step and before water is added thereto.

27. The process of claim 26, wherein the heating step comprises refluxing the first mixture.

28. The process of claim 26, wherein the acetone is removed from the second mixture before the admixing step.

29. The process of claim 26, wherein activated carbon is admixed with, and subsequently removed from, the second mixture.

30. The process of claim 26, comprising adjusting the pH of the second mixture sufficient to precipitate azithromycin.

31. The process of claim 30, wherein the pH of the second mixture is adjusted to about 10 to about 10.5.

32. A process for making azithromycin from desmethyl-azithromycin comprising:

admixing desmethyl-azithromycin, acetone, formaldehyde and formic acid to form a first mixture in which the desmethyl-azithromycin is dissolved;

refluxing the first mixture;

cooling the first mixture to less than about 40° C.;

adding water to the first mixture to form a second mixture;

removing the acetone from the second mixture;

adjusting the pH of the second mixture sufficiently to precipitate azithromycin; and recovering the azithromycin.

33. The process of claim 32, wherein activated carbon is admixed with, and subsequently removed from, the second mixture.

34. A process for making azithromycin monohydrate comprising:

dissolving azithromycin in acetone;

adding a first portion of water to form a first mixture;

maintaining the first mixture at about 40° C.;

adding a second portion of water, thereby initiating precipitation of azithromycin monohydrate;

adding a third portion of water; and optionally cooling the second mixture.

35. The process of claim 34, further comprising recovering azithromycin monohydrate, wherein substantially no azithromycin dihydrate is observed.

36. The process of claim 34, wherein the ratio of the volume of the first portion of water to the volume of the solvent is about 1:5, the ratio of the volume of the second portion of water to the volume of the solvent is about 2:5, and the ratio of the volume of the third portion of water to the volume of the solvent is about 2:5.

37. A process for making azithromycin dihydrate comprising:

dissolving azithromycin in acetone;

adding a first portion of water to the acetone over at least 2 hours to form a mixture;

maintaining the mixture, with optional mixing, for about 4 hours; and adding a second portion of water to the mixture at a rate of up to 0.2 volumes of water per volume of acetone per hour, wherein the temperature is maintained at a temperature ranging from about 20° C. to about 25° C., and wherein the ratio of the volume of the acetone to the total volume of water, after the step of adding the second portion of water, ranges from about 0.5 to 1.5.

* * * * *